Figure 1:
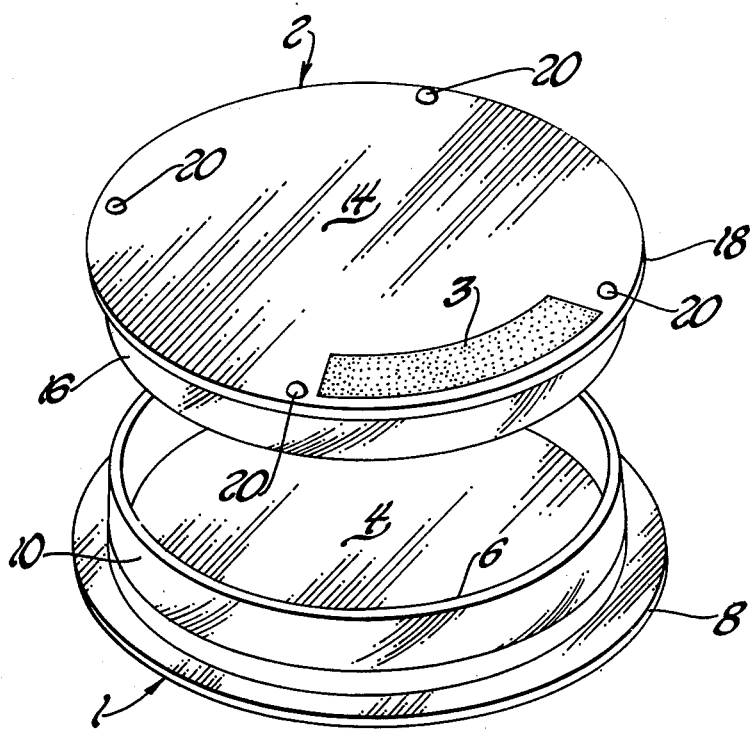

United States Patent [19]

Boomus et al.

[11] 4,160,700

[45] Jul. 10, 1979

[54] PETRI DISH

[75] Inventors: Mary Boomus, Chelsea; Bernard Sobin; John Schweitzer, both of Ann Arbor, all of Mich.

[73] Assignee: Gelman Instrument Company, Ann Arbor, Mich.

[21] Appl. No.: 768,311

[22] Filed: Feb. 14, 1977

[51] Int. Cl.² .............................................. C12B 1/00
[52] U.S. Cl. .................................................. 435/298
[58] Field of Search .............. 195/139, 103.5 M, 127, 195/142; 220/352, 260; 215/295, 298; 23/259

[56] References Cited

U.S. PATENT DOCUMENTS

| | | | |
|---|---|---|---|
| 2,677,646 | 5/1954 | Lovell et al. | 195/139 |
| 2,677,647 | 5/1954 | Lovell | 195/139 |
| 2,780,385 | 2/1957 | Tupper | 220/352 |
| 3,009,564 | 11/1961 | Geloso | 220/352 |
| 3,073,750 | 1/1963 | Greenblatt | 195/139 |
| 3,203,870 | 8/1965 | Andelin | 195/139 |
| 3,234,107 | 2/1966 | Kaufman et al. | 195/139 |
| 3,649,463 | 3/1972 | Buterbaugh | 195/139 |
| 3,684,660 | 8/1972 | Kereluk et al. | 195/139 |
| 3,751,341 | 8/1973 | Seitz et al. | 195/139 |
| 3,928,142 | 12/1975 | Smith | 195/139 |

*Primary Examiner*—R. B. Penland
*Attorney, Agent, or Firm*—Reising, Ethington, Barnard, Perry & Brooks

[57] ABSTRACT

In accordance with the invention there is provided a petri dish comprising a container for the growth of microorganism cultures and a lid for the container to prevent the entrance of contaminants, each of the container and lid having a radially outwardly extending flange, these flanges and the container and lid being so shaped and dimensioned as to enable easy manual removal and reapplication of the lid to the container with the use of only one hand by the person tending to the petri dish thereby leaving the other hand free to administer the microorganism specimen and other ingredients to the dish.

2 Claims, 2 Drawing Figures

U.S. Patent   Jul. 10, 1979   4,160,700

PETRI DISH

The subject matter of the present invention is an improved petri dish characterized in that it is so structured and dimensioned as to enable the biologist, medical technician, or other person using the petri dish to administer to it microorganism specimens and other ingredients with increased rapidity, efficiency, and comfort.

A petri dish of the type to which the present invention relates consists of a container for growing a microorganism culture and a lid for the container with a sufficiently snug fit to prevent the admission of contaminants to the culture. This requirement for a snug fit normally interferes with efficient use of the petri dishes. That is, it is not uncommon for a laboratory to administer the cultures to hundreds or even thousands of the petri dishes in a single day, and this with only one or a few persons to accomplish the task. In using each petri dish, first the lid must be removed, the nutrient broth, microorganism specimen or other ingredient administered to the container, and then the lid replaced onto the container in snug fit thereto. Laboratory efficiency often dictates that hundreds and perhaps as many as a thousand petri dishes be so used by a single technician in a single day. Such efficiency is impossible if the technician must use both hands to remove or replace the lid. Rather, such efficiency is only possible if the technician can rapidly remove and then replace the lid with only one hand, leaving the other hand free to administer the specimen, nutrient or other ingredients to the container. Added to this is a problem of preventing, or at least minimizing discomfort of the technician in accomplishing the task—the discomfort of sore fingers from removing and then replacing hundreds of lids, and to a snug fit, in a single day. Still further adding to the problem is the fact that, to minimize the possibilities of contamination of one culture by another, or by some other contaminant, it has become common practice to use a petri dish only once and then discard it. This dictates that the petri dish be of low cost.

The present invention provides a petri dish which is of sufficiently low cost to enable its discard after only one use, which provides an amply snug fit between the lid and container to prevent contamination, and which enables very fast removal and replacement of the lid with the use of only one hand by the technician, and with minimum possibility of discomfort to the technician by reason of such task no matter that the technician so administer to hundreds of the petri dishes in a single day.

Figure 2:
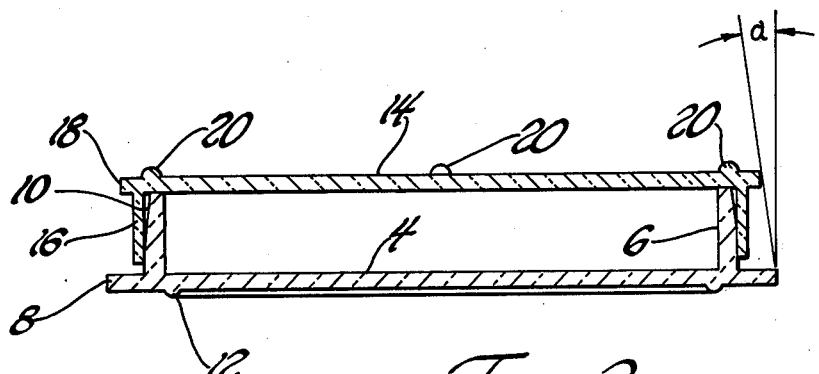

The aforesaid features and advantages of the invention will appear more clearly from the following detailed description of a preferred embodiment thereof made with reference to the accompanying drawings wherein:

FIG. 1 is a perspective view of a petri dish made in accordance with the invention and shown with the lid separated from the container; and FIG. 2 is a side view in section of the petri dish shown in FIG. 1 but with the lid assembled to the container.

Referring now to the drawings, the petri dish consists of a container 1 and a lid 2 for the container, each of these parts being of organic resin and of unitary molded construction. At least the lid 2 should be transparent to enable inspection of the culture grown in the petri dish and it is preferred that both the lid and the container be molded of a transparent organic resin such as transparent polystyrene. A small portion 3 of the upper surface of the lid can be molded to a frosted finish so as to enable easy pencil or pen marking of the petri dish for identification of the culture being grown therein.

The container has a flat, round bottom wall 4 from which there extends perpendicularly upwardly a substantially cylindrical side wall 6. Extending radially outwardly from and substantially coplanar with the bottom wall 4 is a circular flange 8. The outer surface of the side wall is tapered inwardly at its upper extremity, as shown at 10, whereby this upper portion of the outer surface of side wall 6 is of frustoconical shape. The side wall 6 should have an outer diameter, at the bottom, non-tapered portion thereof, of from about one to four inches and a height of from about $\frac{1}{4}$ to $\frac{1}{2}$ inch, and the circular flange 8 should have an outer diameter which is about $\frac{1}{4}$ to $\frac{3}{4}$ inch greater than the aforesaid diameter of the outer surface of the side wall.

Extending downwardly from the bottom wall of the container is a circular projection 12 of arcuate cross-section, this circular projection being concentric with the side wall 6 and the flange 8 and, in the embodiment shown, being of slightly less diameter than that of the side wall 6. In the embodiment shown the depth of the projection 12 is approximately 1/64 inch.

The lid 2 of the petri dish has a flat, round top wall 14 which has extending perpendicularly downwardly therefrom a substantially cylindrical side wall 16 having a depth less than the height of side wall 6 of the container. Extending radially outwardly from a substantially coplanar with the top wall 14 is a circular flange 18 having an outer diameter substantially less than the outer diameter of the flange 8 of the container. More specifically, the outside diameter of the flange 18 should be sufficiently less than the outside diameter of the flange 8 that when the lid is assembled to the container, as shown in FIG. 2, the angle α (see FIG. 2) is from about 5° to 30°. The angle α is the angle, in a vertical plane, between the longitudinal axes of the dish and the line joining the edges of the flanges 8 and 18.

The inner surface of the side wall 16 of the lid has a diameter about the same as the outer diameter of the bottom, non-tapered portion of the side wall 6 of the container such that when the lid is placed on the container, as shown in FIG. 2, there is a snug fit so as to assure against the entrance of contaminants.

Extending upwardly from the top of the lid are four equally circumferentially spaced projections 20 which can be quite small in height—less than 1/64 inch in the particular embodiment shown. The projections 20 define a circle of slightly less diameter than that of downwardly extending projection 12 on the container. The function of the projections 20 and the projection 12 is to enable the assembled petri dishes to be stacked one on top of the other in axial alignment, the projections 20 of one petri dish mating with the projection 12 of the next-above petri dish thereby to maintain the axial alignment and the stability of the stack. Such projections are preferred, to enable easy stacking of the petri dishes, but are not essential.

The tapered upper portion of the cylindrical side wall 6 of the container enables and expedites easy manual insertion of the lid onto the container. It will be understood, of course, that additionally or alternatively this function can be attained by tapering, to frustoconical shape, the inner surface of the side wall 16 of the lid.

But cardinal to the attainment of the advantages of the petri dishes of the present invention are the flanges 8 and 18 and the relative dimensioning thereof along with the dimensioning of the overall container and lid. That is, because of the structure and dimensioning, a technician using but two or more fingers of a single hand can rapidly, and without great effort or discomfort, lift the lid from the container and then replace the lid onto the container in snugly fitted relationship. By way of the relative dimensioning of the flanges 8 and 18, as described, it is simply a matter of placing the tips of two or more fingers of a single hand against the flange 8 and then gently squeezing the hand whereby the fingers contact the flange 18 and thereby lift the lid away from the container. Replacement of the lid onto the container is equally simple and comfortable.

It will be understood that while the invention has been described in detail with reference to a particular embodiment thereof, various changes and modifications can be made all within the full and intended scope of the following claims.

What is claimed is:
1. A petri dish comprising:
   a molded, unitary organic resin container having a substantially flat, round bottom wall and a substantially cylindrical side wall extending perpendicularly upwardly from said bottom wall, said side wall having a height of from about ¼ to ½ inch and having an outer cylindrical surface with a diameter of from about one to four inches, said container having a circular flange extending radially outwardly from and substantially coplanar with said bottom wall, said flange having and outer diameter about ¼ to ¾ inch greater than the diameter of the outer surface of said side wall;
   and a molded, unitary, transparent organic resin lid for said container having a round top wall and a substantially cylindrical side wall extending perpendicularly downwardly from said top wall, said downwardly extending side wall of said lid having an inner cylindrical surface with a diameter about the same as the diameter of the outer surface of said upwardly extending side wall of said container such that said inner cylindrical surface of said downwardly extending side wall of said lid fits snugly against said outer cylindrical surface of said upwardly extending side wall of said container to assure against the entrance of contaminants into said container, said lid having a circular flange extending radially outwardly from and substantially coplanar with said top wall, said flange on said lid having an outer diameter less than the outer diameter of said flange on said container;
   at least one of said cylindrical surfaces being tapered adjacent the extremity thereof thereby to enable said lid to be easily fitted onto said container.
2. A petri dish as set forth in claim 1 wherein the angle in a vertical plane between the longitudinal axis of the dish and a line joining the edges of the flanges on the container and lid is from about 5° to 30°.

* * * * *